(12) United States Patent
Fortin

(10) Patent No.: US 10,716,776 B2
(45) Date of Patent: Jul. 21, 2020

(54) POLYUNSATURATED FATTY ACID MONOGLYCERIDES, COMPOSITIONS, METHODS AND USES THEREOF

(71) Applicant: SCF PHARMA INC., Sainte-Luce (CA)

(72) Inventor: Samuel C. Fortin, Sainte-Luce (CA)

(73) Assignee: SCF PHARMA INC., Sainte-Luce (CA)

( * ) Notice: Subject to any disclaimer, the term of this patent is extended or adjusted under 35 U.S.C. 154(b) by 0 days.

(21) Appl. No.: 16/517,607

(22) Filed: Jul. 21, 2019

(65) Prior Publication Data

US 2020/0016112 A1 Jan. 16, 2020

Related U.S. Application Data

(63) Continuation-in-part of application No. PCT/CA2019/050139, filed on Feb. 4, 2019.

(60) Provisional application No. 62/627,244, filed on Feb. 7, 2018.

(51) Int. Cl.
*A61K 36/00* (2006.01)
*A61K 31/232* (2006.01)
*A61K 31/05* (2006.01)
*A61K 31/192* (2006.01)
*A61K 31/352* (2006.01)
*A61K 35/60* (2006.01)
*A61K 36/185* (2006.01)

(52) U.S. Cl.
CPC ............ *A61K 31/232* (2013.01); *A61K 31/05* (2013.01); *A61K 31/192* (2013.01); *A61K 31/352* (2013.01); *A61K 35/60* (2013.01); *A61K 36/185* (2013.01)

(58) Field of Classification Search
CPC ...................................................... A61K 36/00
USPC ........................................................ 424/725
See application file for complete search history.

(56) References Cited

U.S. PATENT DOCUMENTS

2018/0264121 A1* 9/2018 Donaduzzi .............. A61P 25/22

* cited by examiner

*Primary Examiner* — Michael V Meller
(74) *Attorney, Agent, or Firm* — Bereskin & Parr LLP/S.E.N.C.R.L., s.r.l.

(57) ABSTRACT

There are provided various compounds and compositions comprising polyunsaturated fatty acid monoglycerides and derivatives thereof. These compounds and compositions can be useful for increasing the life span of a subject; for increasing the disability-free life expectancy, for slowing down the ageing process of a subject; for increasing the mitochondrial OXPHOS of a subject; for decreasing the mitochondrial LEAK of a subject; for increasing the mitochondrial RCR or COUPLING EFFICIENCY of a subject; and for optimizing the mitochondrial functions of a subject. These compounds and compositions comprise at least one compound chosen from

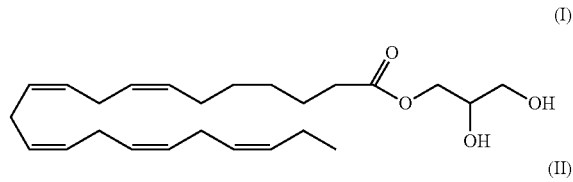

(I)

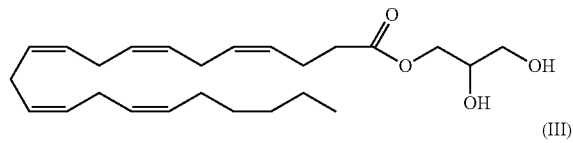

(II)

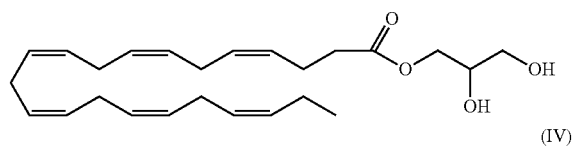

(III)

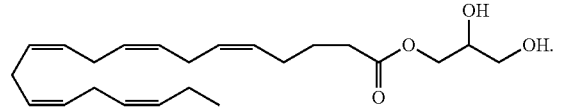

(IV)

1 Claim, 13 Drawing Sheets

POLYUNSATURATED FATTY ACID MONOGLYCERIDES, COMPOSITIONS, METHODS AND USES THEREOF

CROSS-REFERENCE TO RELATED APPLICATIONS

The present application is a continuation-in-part of International patent application no. PCT/CA2019/050139, filed on Feb. 4, 2019, which claims priority to U.S. application No. 62/627,244 filed on Feb. 7, 2018. These documents are hereby incorporated by reference in their entirety.

FIELD OF THE DISCLOSURE

The present document relates to the field of chemical biology. More particularly, it relates to polyunsaturated fatty acid monoglyceride compounds and combinations thereof. It also provides methods for increasing the lifespan and/or slowing down the ageing process of a subject in need thereof. There is also provided a method for enhancing and/or optimizing the mitochondrial functions of a subject in need thereof by decreasing the mitochondrial proton LEAK and/or increasing the mitochondrial OXPHOS and/or increasing the COUPLING EFFICIENCY.

BACKGROUND OF THE DISCLOSURE

The normal functions of an organism gradually decline with ageing and the exact mechanism are not totally understood. One consensus upon almost all specialists is that mitochondria are involved in the ageing process (Payne, B. A. I. and P. F. Chinnery. 2015 "Mitochondrial dysfunction in aging: Much progress but many unresolved questions." Biochimica et Biophysica Acta 1847; 11: 1347-1353).

SUMMARY OF THE DISCLOSURE

According to one aspect there is provided at least one compound chosen from compound of formula (I), compound of formula (II), compound of formula (III) and compound of formula (IV):

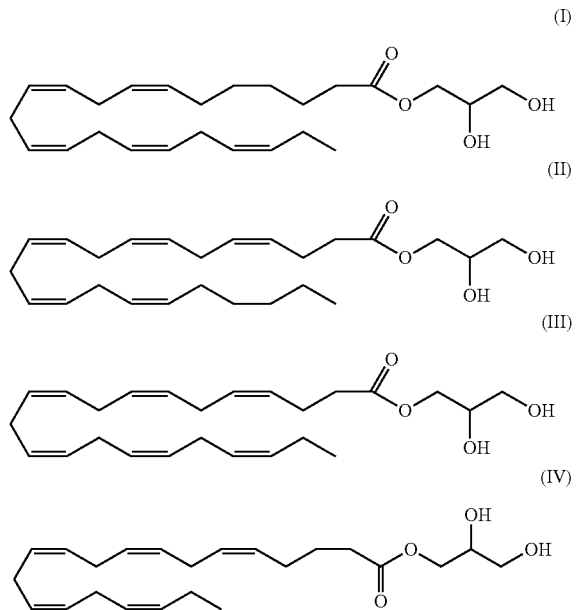

for increasing the life span of a subject in need thereof.

According to another aspect there is provided at least one compound chosen from compound of formula (I), compound of formula (II), compound of formula (III) and compound of formula (IV) for increasing of the disability-free life expectancy of a subject in need thereof.

According to another aspect there is provided at least one compound chosen from compound of formula (I), compound of formula (II), compound of formula (III) and compound of formula (IV) for slowing down the ageing process of a subject in need thereof.

According to another aspect there is provided at least one compound chosen from compound of formula (I), compound of formula (II), compound of formula (III) and compound of formula (IV) for increasing the mitochondrial OXPHOS of a subject in need thereof.

According to another aspect there is provided at least one compound chosen from compound of formula (I), compound of formula (II), compound of formula (III) and compound of formula (IV) for decreasing the mitochondrial LEAK of a subject in need thereof.

According to another aspect there is provided at least one compound chosen from compound of formula (I), compound of formula (II), compound of formula (III) and compound of formula (IV) for increasing the mitochondrial RCR or COUPLING EFFICIENCY of a subject in need thereof.

According to another aspect there is provided at least one compound chosen from compound of formula (I), compound of formula (II), compound of formula (III) and compound of formula (IV) for optimizing the mitochondrial functions of a subject in need thereof.

According to another aspect there is provided the use of at least one compound chosen from compound of formula (I), compound of formula (II), compound of formula (III) and compound of formula (IV) for increasing the life span of a subject in need thereof.

According to another aspect there is provided the use of at least one compound chosen from compound of formula (I), compound of formula (II), compound of formula (III) and compound of formula (IV) for increasing of the disability-free life expectancy of a subject in need thereof.

According to another aspect there is provided the use of at least one compound chosen from compound of formula (I), compound of formula (II), compound of formula (III) and compound of formula (IV) for slowing down the ageing process of a subject in need thereof.

According to another aspect there is provided the use of at least one compound chosen from compound of formula (I), compound of formula (II), compound of formula (III) and compound of formula (IV) for increasing the mitochondrial OXPHOS of a subject in need thereof.

According to another aspect there is provided the use of at least one compound chosen from compound of formula (I), compound of formula (II), compound of formula (III) and compound of formula (IV) for decreasing the mitochondrial LEAK of a subject in need thereof.

According to another aspect there is provided the use of at least one compound chosen from compound of formula (I), compound of formula (II), compound of formula (III) and compound of formula (IV) for increasing the mitochondrial RCR or COUPLING EFFICIENCY of a subject in need thereof.

According to another aspect there is provided the use of at least one compound chosen from compound of formula (I), compound of formula (II), compound of formula (III)

and compound of formula (IV) for optimizing the mitochondrial functions of a subject in need thereof.

According to another aspect there is provided the use of at least one compound chosen from compound of formula (I), compound of formula (II), compound of formula (III) and compound of formula (IV) in the manufacture of a medicament for increasing the life span of a subject in need thereof.

According to another aspect there is provided the use of at least one compound chosen from compound of formula (I), compound of formula (II), compound of formula (III) and compound of formula (IV) in the manufacture of a medicament for increasing of the disability-free life expectancy of a subject in need thereof.

According to another aspect there is provided the use of at least one compound chosen from compound of formula (I), compound of formula (II), compound of formula (III) and compound of formula (IV) in the manufacture of a medicament for slowing down the ageing process of a subject in need thereof.

According to another aspect there is provided the use of at least one compound chosen from compound of formula (I), compound of formula (II), compound of formula (III) and compound of formula (IV) in the manufacture of a medicament for increasing the mitochondrial OXPHOS of a subject in need thereof.

According to another aspect there is provided the use of at least one compound chosen from compound of formula (I), compound of formula (II), compound of formula (III) and compound of formula (IV) in the manufacture of a medicament for decreasing the mitochondrial LEAK of a subject in need thereof.

According to another aspect there is provided the use of at least one compound chosen from compound of formula (I), compound of formula (II), compound of formula (III) and compound of formula (IV) in the manufacture of a medicament for increasing the mitochondrial RCR or COUPLING EFFICIENCY of a subject in need thereof.

According to another aspect there is provided the use of at least one compound chosen from compound of formula (I), compound of formula (II), compound of formula (III) and compound of formula (IV) in the manufacture of a medicament for optimizing the mitochondrial functions of a subject in need thereof.

According to another aspect there is provided a method for increasing the life span of a subject in need thereof comprising administering an effective amount of at least one compound chosen from compound of formula (I), compound of formula (II), compound of formula (III) and compound of formula (IV).

According to another aspect there is provided a method for increasing of the disability-free life expectancy of a subject in need thereof comprising administering to the subject an effective amount of at least one compound chosen from compound of formula (I), compound of formula (II), compound of formula (III) and compound of formula (IV).

According to another aspect there is provided a method for slowing down the ageing process of a subject in need thereof comprising administering to the subject an effective amount of at least one compound chosen from compound of formula (I), compound of formula (II), compound of formula (III) and compound of formula (IV).

According to another aspect there is provided a method for increasing the mitochondrial OXPHOS of a subject in need thereof comprising administering to the subject an effective amount of at least one compound chosen from compound of formula (I), compound of formula (II), compound of formula (III) and compound of formula (IV).

According to another aspect there is provided a method for decreasing the mitochondrial LEAK of a subject in need thereof of a subject in need thereof comprising administering to the subject an effective amount of at least one compound chosen from compound of formula (I), compound of formula (II), compound of formula (III) and compound of formula (IV).

According to another aspect there is provided a method for increasing the mitochondrial RCR or COUPLING EFFICIENCY of a subject in need thereof comprising administering to the subject an effective amount of at least one compound chosen from compound of formula (I), compound of formula (II), compound of formula (III) and compound of formula (IV).

According to another aspect there is provided a method for optimizing the mitochondrial functions of a subject in need thereof comprising administering to the subject an effective amount of at least one compound chosen from compound of formula (I), compound of formula (II), compound of formula (III) and compound of formula (IV).

According to another aspect, there is provided a composition comprising:
(i) at least one compound chosen from compound of formula (I), compound of formula (II), compound of formula (III) and compound of formula (IV);
(ii) at least one ingredient chosen from lipids, a $C_{10}$ saturated rich oils, selenium, vitamin B and cannabinoids.

According to another aspect, there is provided a composition comprising (i) at least one compound chosen from compound of formula (I), compound of formula (II), compound of formula (III) and compound of formula (IV) at compounds and (ii) at least one of a lipid and $C_{10}$ saturated rich oil for increasing the life span or the disability-free life expectancy of a subject in need thereof According to another aspect, there is provided a composition comprising (i) at least one compound chosen from compound of formula (I), compound of formula (II), compound of formula (III) and compound of formula (IV) at compounds and (ii) at least one of a lipid and selenium for increasing the life span or the disability-free life expectancy of a subject in need thereof.

According to another aspect, there is provided a composition comprising (i) at least one compound chosen from compound of formula (I), compound of formula (II), compound of formula (III) and compound of formula (IV) at compounds and (ii) at least one a lipid and vitamin B for increasing the life span or the disability-free life expectancy of a subject in need thereof.

According to another aspect, there is provided a composition comprising (i) at least one compound chosen from compound of formula (I), compound of formula (II), compound of formula (III) and compound of formula (IV) at compounds and (ii) at least one of a lipid and a cannabinoid for increasing the life span or the disability-free life expectancy of a subject in need thereof.

BRIEF DESCRIPTION OF THE FIGURES

Further features and advantages will become more readily apparent from the following description of specific embodiments as illustrated by way of examples in the appended figures wherein.

DETAILED DESCRIPTION OF THE DISCLOSURE

Figure 1:
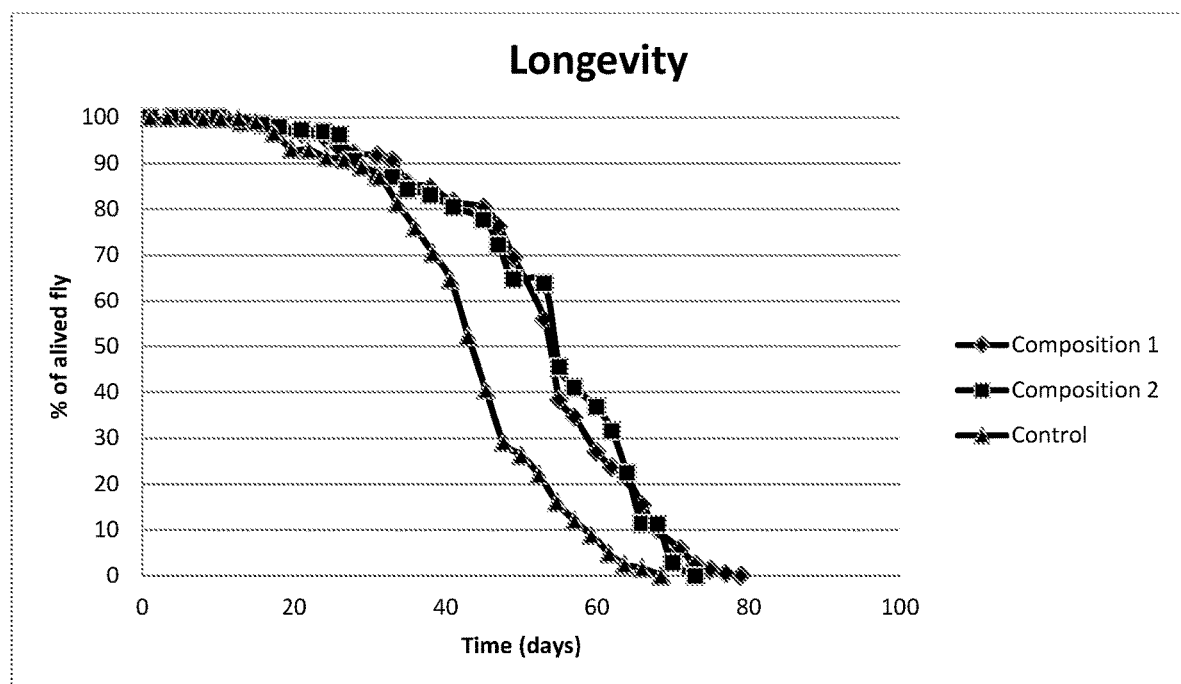
FIG. 1 represents the survival curve of *Drosophila melanogaster* males fed a standard diet (SD), a standard diet supplemented with composition 1, and a standard diet supplemented with composition 2. Results are presented as the percentage of *Drosophila* alive counted every 2-3 days (N>145 for each group).

Further features and advantages of the previously-mentioned compounds will become more readily apparent from the following description of non-limiting examples.

The term "OXPHOS" as used herein refers to oxidative phosphorylation that is the metabolic pathway in which cells use enzymes to oxidize nutrients, thereby releasing energy which is used to produce adenosine triphosphate (ATP).

The term "LEAK" as used herein refers to a leak of protons that occurs across the mitochondrial inner membranes of eukaryotic cells.

The term "RCR" or "COUPLING EFFICIENCY" or "RESPIRATORY ACCEPTOR CONTROL RATIO" as used herein refers to a value calculated by OXPHOS/LEAK or state 3/state 4.

The term "lipid" as used herein refers to as any fat-soluble (lipophilic), molecules, such as fats, fat-like substances, oils (such as animal oil, marine oil or vegetable oil), waxes, sterols (such as cholesterol, ergosterol, sitosterol, stigmasterol, fat-soluble vitamins (such as vitamins A, D, E and K), fatty acids, oxidized fatty acid (such as lipoxin, specialized pro-resolving mediators or epoxydes), fatty acids esters thereof, and various derivatives thereof such as monoglycerides, diglycerides, triglycerides, phospholipids, glycolipids, and cerebrosides and pharmaceutically acceptable salts thereof.

The term "selenium" as used herein refers to mineral form such as selenates, selenides, selenites or selenocyanate or organoselenium form such as selenols, selenonic acid, seleno amino acids or selenoproteins.

The term "vitamin B" as used herein refers to vitamin B1 (thiamine), vitamin B2 (riboflavin), vitamin B3 (niacin or nicotinamide riboside, vitamin B5 (pantothenic acid), vitamin B6 (pyridoxine, pyridoxal, pyridoxamine), vitamin B7 (biotin), vitamin B9 (folate) or vitamin B12 (cobalam ins).

The term "cannabinoids" as used herein refers to THC (Tetrahydrocannabinol), THCA (Tetrahydrocannabinolic acid), CBD (Cannabidiol), CBDA (Cannabidiolic Acid), CBN (Cannabinol), CBG (Cannabigerol), CBC (Cannabichromene), CBL (Cannabicyclol), CBV (Cannabivarin), THCV (Tetrahydrocannabivarin), CBDV, (Cannabidivarin), CBCV (Cannabichromevarin), CBGV (Cannabigerovarin), CBGM, (Cannabigerol Monomethyl Ether), CBE (Cannabielsoin) or CBT (Cannabicitran).

The expression "life span" as used herein refers to Maximum life span (the maximum lifespan observed in a group), the Life expectancy (the average lifespan expected of a group) or the Longevity, (the average lifespan expected under ideal conditions).

The expression "disability-free life expectancy" as used herein refers to the Healthy Life Years (HLY) indicator (also called disability-free life expectancy) that measures the number of remaining years that a person of a certain age is still supposed to live without disability.

The expression "effective amount" of a compound of the present disclosure is a quantity sufficient to, when administered to the subject, including a mammal, for example a human, effect beneficial or desired results, including clinical results, and, as such, an "effective amount" depends upon the context in which it is being applied. The amount of a given compound of the present disclosure that will correspond to such an amount will vary depending upon various factors, such as the given drug or compound, the pharmaceutical formulation, the route of administration, the identity of the subject or host being treated, and the like, but can nevertheless be routinely determined by one skilled in the art.

For example, the subject in need thereof can be a bee, human, cat, dog, etc. . . . .

For example, the at least one compound is said compound of formula (I).

For example, the at least one compound is said compound of formula (II).

For example, the at least one compound is said compound of formula (III).

For example, the at least one compound is said compound of formula (IV).

For example, the at least one compound is said compound of formula (I), said compound of formula (III) and said compound of formula (IV).

For example, the at least one compound is said compound of formula (I) and said compound of formula (IV).

For example, the at least one compound is said compound of formula (I) and said compound of formula (III).

For example, the at least one compound is said compound of formula (III) and said compound of formula (IV).

For example, the at least one compound can be for use in combination with at least one ingredient chosen from lipids, a $C_{10}$ saturated rich oils, selenium, vitamin B and cannabinoids.

For example, the at least one ingredient and said at least one compound can be for simultaneous administration.

For example, the at least one ingredient and said at least one compound can be for separate administration.

For example, the at least one compound chosen from compound of formula (I), compound of formula (II), compound of formula (III) and compound of formula (IV) can be administered in combination with at least one ingredient chosen from lipids, a $C_{10}$ saturated rich oils, selenium, vitamin B and cannabinoids.

For example, the at least one ingredient and said at least one compound can be administered simultaneously.

For example, the at least one ingredient and said at least one compound can be administered separately.

Further features and advantages of the previously-mentioned compounds will become more readily apparent from the following description of non-limiting examples.

Example 1

Preparation of a Composition (Composition 1) Comprising Compound III.

Composition 1 comprising compound IV, was prepared by reacting 1 kg of EPA concentrated fish oil (ethyl ester form) with 0.27 kg of glycerol with 0.05 kg of Novozym 435 (lipase) in 2 kg of acetone at 50° C. for 4 h. The lipase was filtered, the acetone was removed in vacuo and the mixture was allowed to stand for phase separation. The lower unreacted glycerol phase was removed to give 1 kg of the final composition 1 comprising compound IV, unreacted ethyl ester and small amount of diglycerides and triglyceride.

Example 2

Preparation of a Composition (Composition 2) Comprising Compound II.

Composition 2 comprising compound III, was prepared by reacting 1 kg of DHA concentrated fish oil (ethyl ester form) with 0.27 kg of glycerol with 0.05 kg of Novozym 435 (lipase) in 2 kg of acetone at 50° C. for 4 h. The lipase was filtered, the acetone was removed in vacuo and the mixture was allowed to stand for phase separation. The lower unreacted glycerol phase was removed to give 1 kg of the final composition 2 comprising compound III, unreacted ethyl ester and small amount of diglycerides and triglyceride.

Example 3

Figure 2:
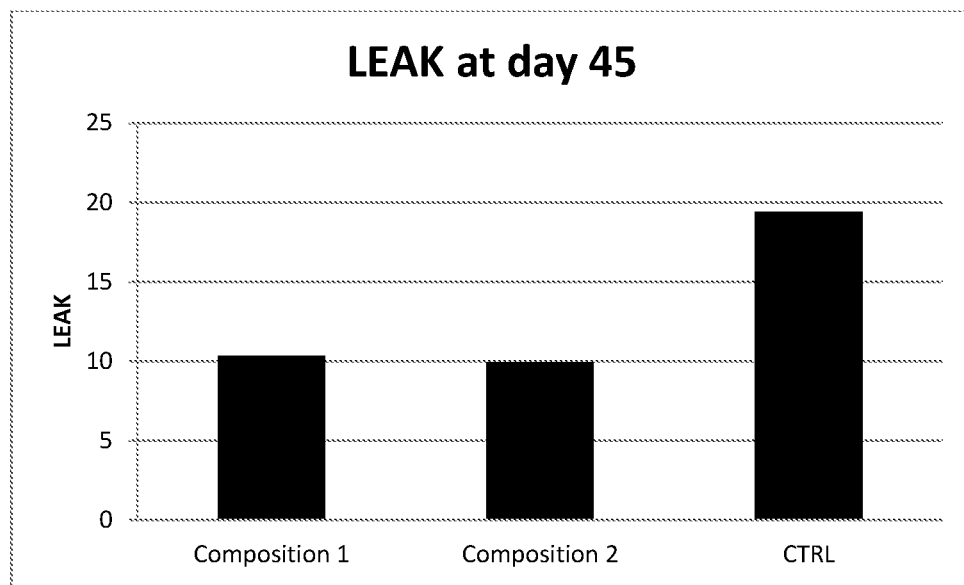
FIG. 2 represents the effects of composition 1 and composition 2 on mass-specific mitochondrial LEAK of thorax muscle from *Drosophila melanogaster* at day 45.
Figure 3:
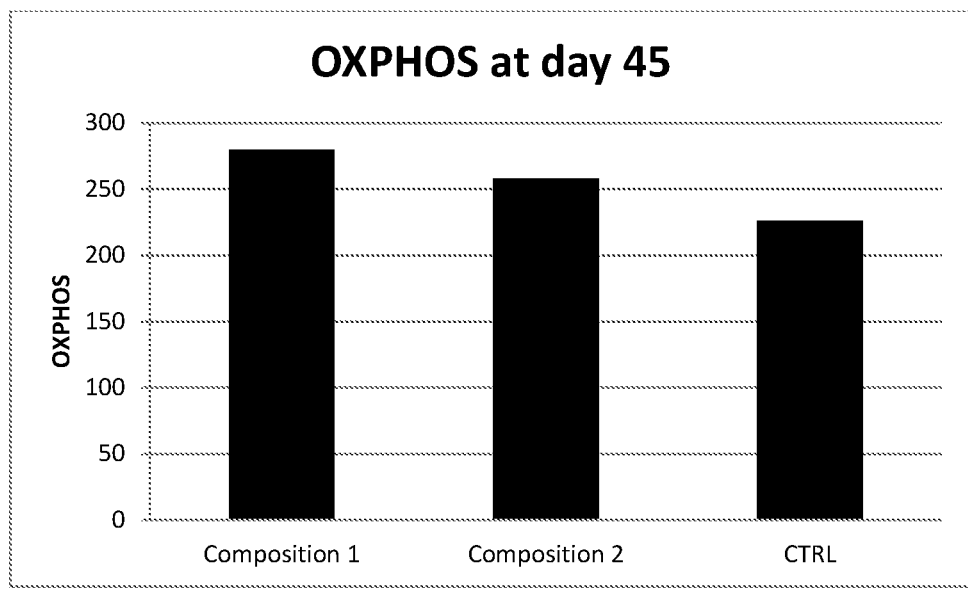
FIG. 3 represents the effects of composition 1 and composition 2 on mass-specific mitochondrial OXPHOS of thorax muscle from *Drosophila melanogaster* at day 45.

Composition 1 and Composition 2 Extend Longevity in *D. Melanogaster* by Decreasing the LEAK, Increasing the OXPHOS and Increasing COUPLING EFFICIENCY Male *drosophila* (strain w1118, Bloomington *Drosophila* Stock Center, Bloomington, Ind., USA) were collected on the day of hatching and were fed a standard cornmeal diet (SD), or a SD supplemented with 0.3 mg·mL-1 of a formulation containing composition 1 or composition 2. The longevity is presented in FIG. 1 and was evaluated by recording the survival of flies every 2-3 days (N>145, in triplicates). The three groups were significantly different from each other (log-rank $X^2=16.5$, P<0.001 between SD and composition 2; log-rank $X^2=48.3$, P<0.001 between SD and composition 1; log-rank $X^2=9.8$, P=0.002 between composition 2 and composition 1). Specifically, median lifespans were similar between composition 2 and composition 1 (55 days) and both were higher than when the flies were fed the SD (48 days). Maximal lifespan was however the highest with composition 1 (79 days), followed by composition 2 (73 days) and SD (68.5 days). Mitochondrial oxygen consumption was evaluated in permeabilized thorax of *Drosophila* at 45 days old, N=5-6 for each dietary treatment. LEAK of *Drosophila* fed either composition 1 or composition 2 were lower than with the SD, FIG. 2. Moreover, flies fed composition 1 presented higher OXPHOS than SD FIG. 3.

Figure 4:
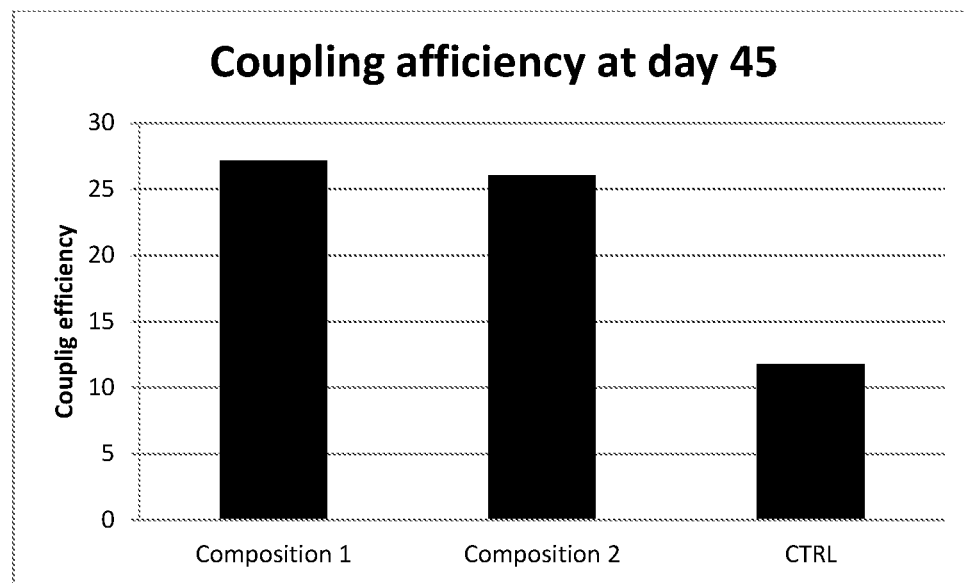
FIG. 4 represents the effects of composition 1 and composition 2 on mass-specific mitochondrial COUPLING EFFICIENCY of thorax muscle from *Drosophila melanogaster* at day 45.

Both composition 1 and composition 2 also had higher COUPLING EFFICIENCY than SD, and composition 1 presented higher COUPLING EFFICIENCY than composition 2 FIG. 4)

Example 4

Composition 1 Decreases Mitochondrial Proton Leak, Increase the OXPHOS and Ameliorate the COUPLING EFFICIENCY in a Pilot Human Clinical Trial.

Figure 5:
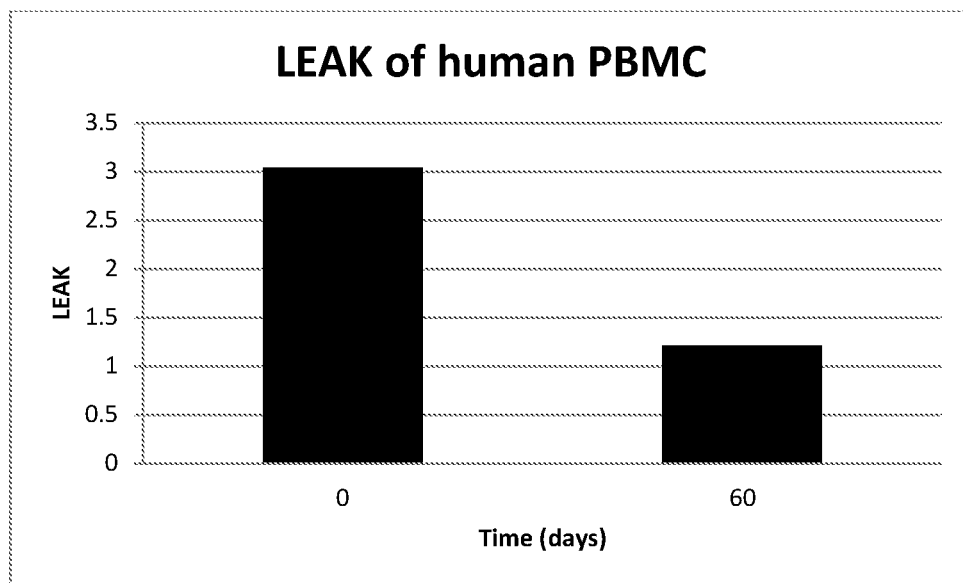
FIG. 5 represents the variation of the LEAK of the PBMC at T=0 and T=60 days.
Figure 6:
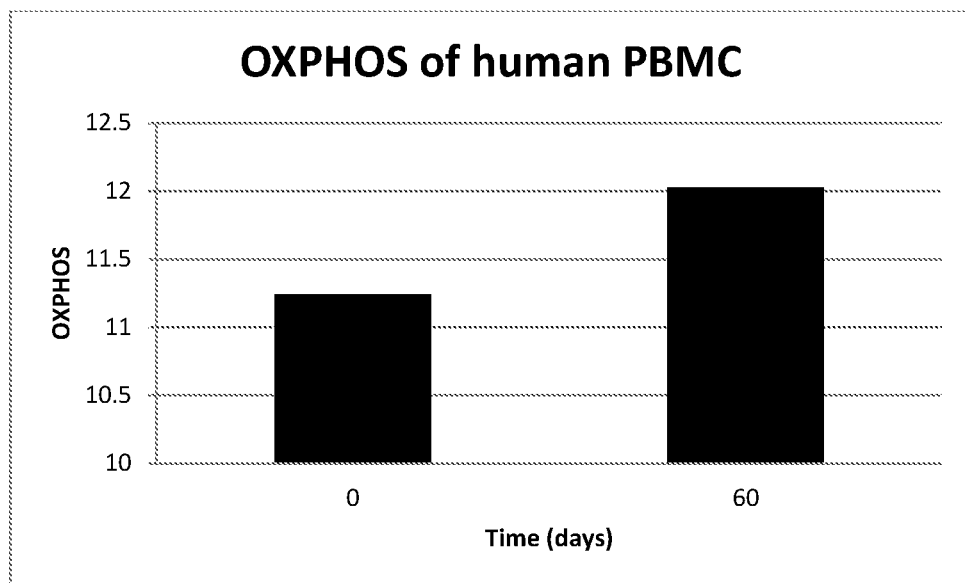
FIG. 6 represents the variation of the OXPHOS of the PBMC at T=0 and T=60 days.
Figure 7:
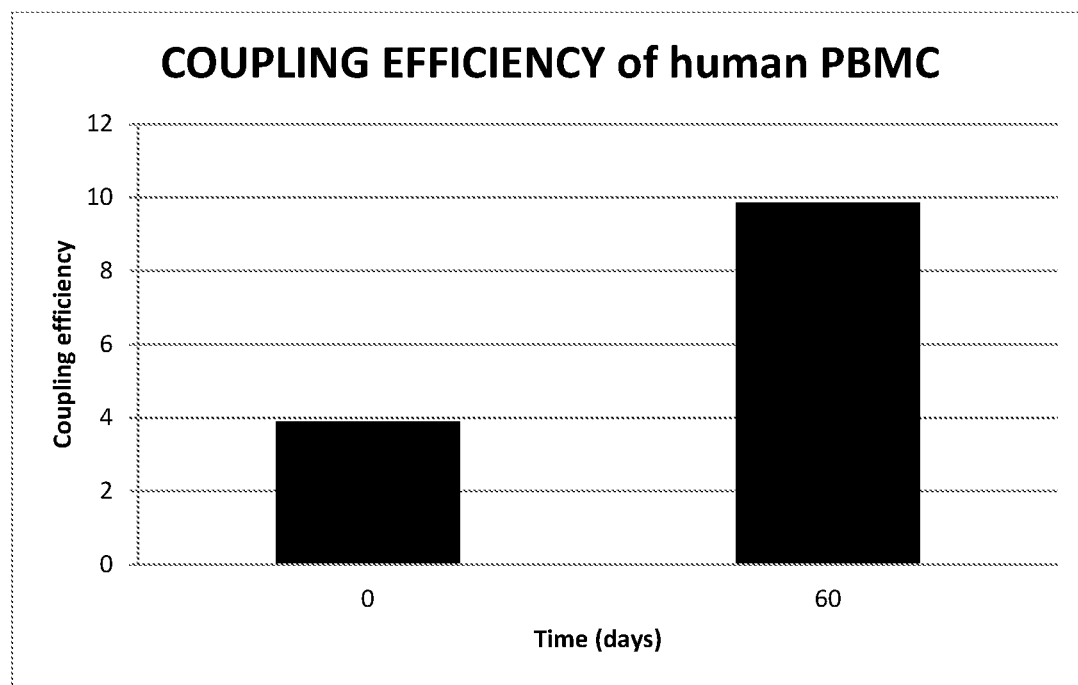
FIG. 7 represents the variation of the COUPLING EFFICIENCY of the PBMC at T=0 and T=60 days.

Four patients were recruited at SCF Pharma and the study was approved by a review boards. Prior to participation, all subjects signed a written informed consent form previously reviewed and discussed with a study investigator. Eligible subjects received composition 1 (1.5 g) for 60 days. The mean LEAK of the PBMC cells of the patients at T=0 (3.04) and T=60 days (1.21) is presented in FIG. 5, the mean OXPHOS of the PBMC cells of the patients at T=0 (11,24) and T=60 days (12,03) is presented in FIG. 6, and the mean COUPLING EFFICIENCY of the PBMC cells of the patients at T=0 (3.89) and T=60 days (9.86) is presented in FIG. 7

While the compounds, compositions, methods and uses thereof have been described in connection with specific embodiments thereof, it will be understood that they can be further modified and this application is intended to cover any variations, uses, or adaptations of the compounds, compositions, methods and uses thereof following, in general, the principles described in the present document and including such departures from the present disclosure as come within known or customary practice within the art to which the present document pertains and as may be applied to the features hereinbefore set forth, and as follows in the scope of the appended claims.

Example 5

Composition 1 Decreases Mitochondrial Proton Leak, Increase the OXPHOS and Ameliorate the COUPLING EFFICIENCY in a Second Pilot Human Clinical Trial.

Figure 8:
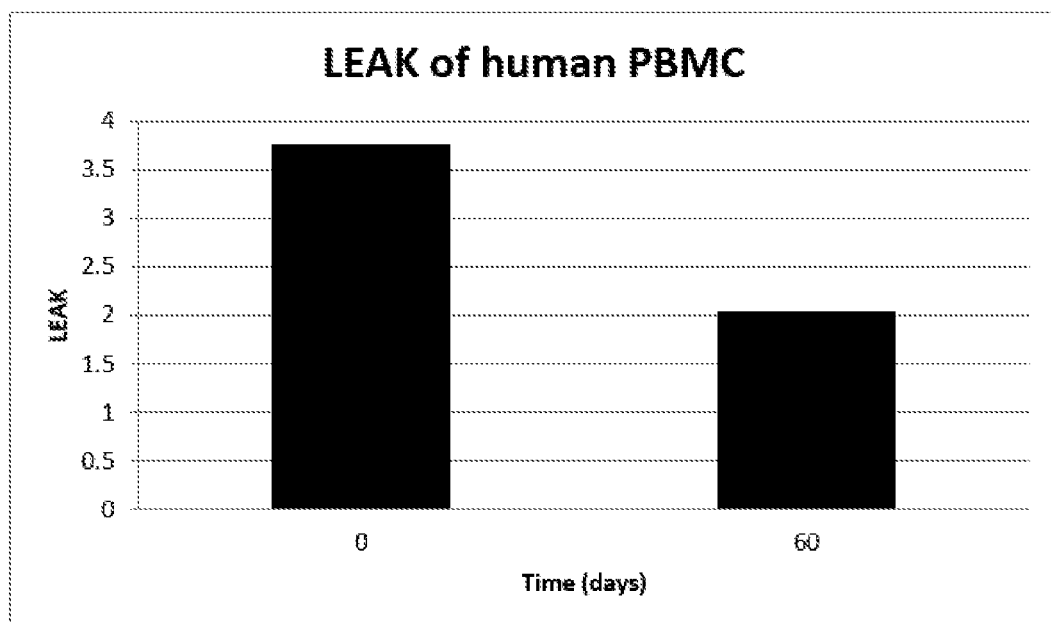
FIG. 8 represents the variation of the LEAK of the PBMC at T=0 and T=60 days.
Figure 9:
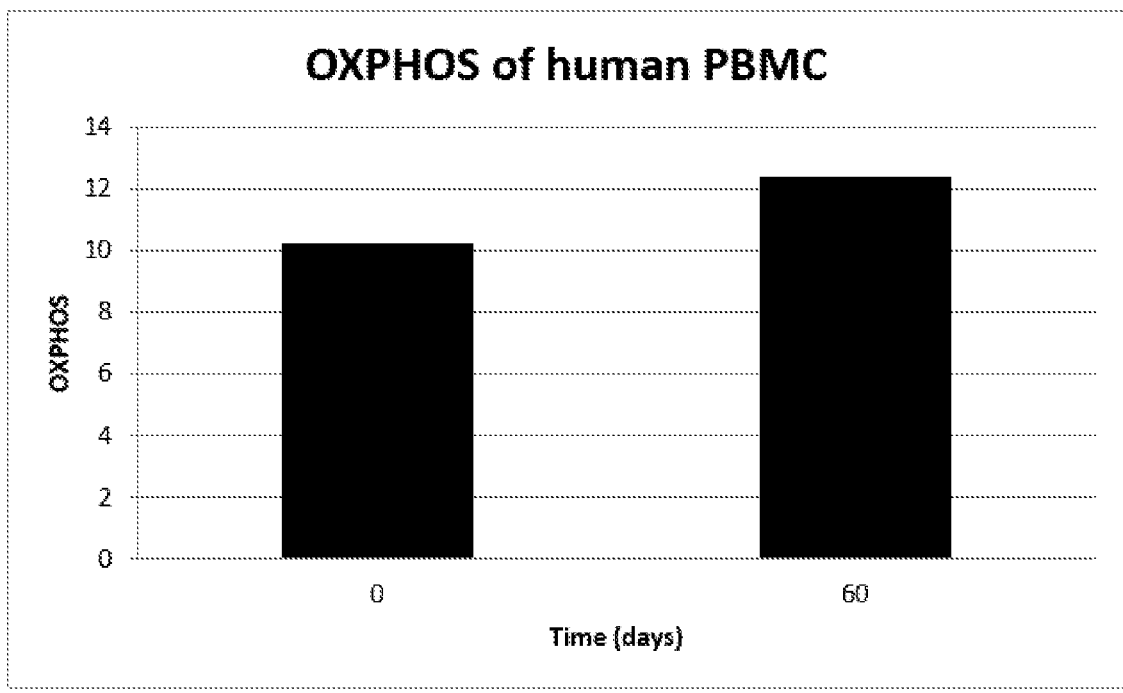
FIG. 9 represents the variation of the OXPHOS of the PBMC at T=0 and T=60 days.
Figure 10:
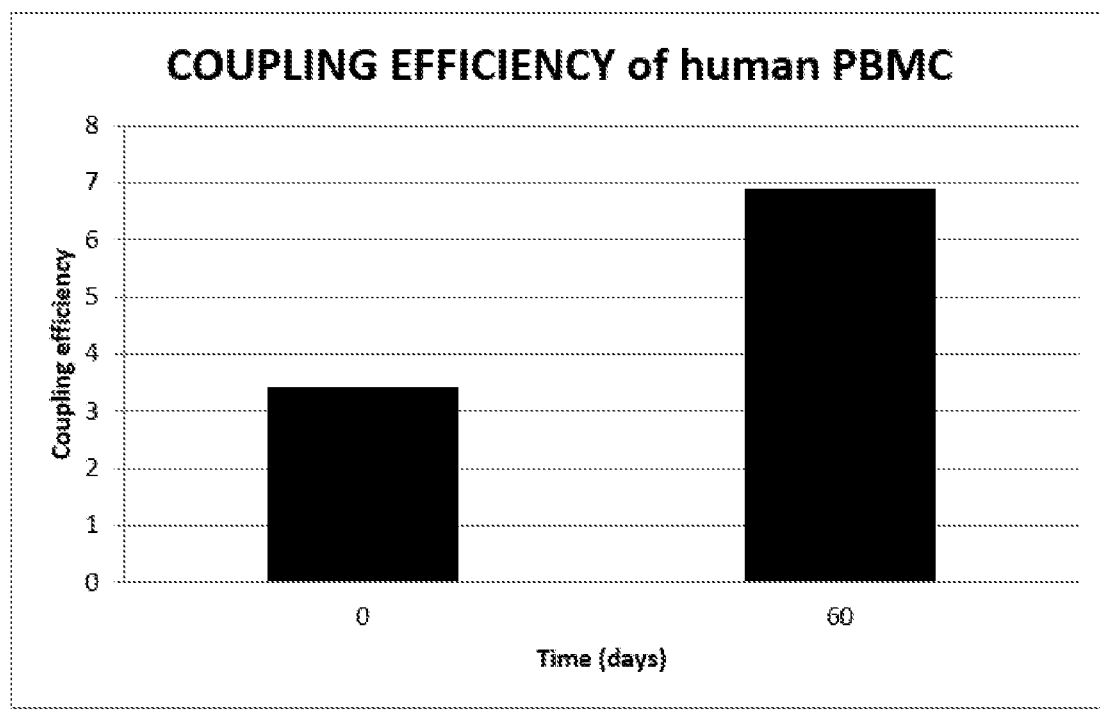
FIG. 10 represents the variation of the COUPLING EFFICIENCY of the PBMC at T=0 and T=60 days.

Six patients were recruited at SCF Pharma and the study was approved by a review boards. Prior to participation, all subjects signed a written informed consent form previously reviewed and discussed with a study investigator. Eligible subjects received composition 1 (1.5 g) for 60 days. The mean LEAK of the PBMC cells of the patients at T=0 (3.76) and T=60 days (2.04) is presented in FIG. 8, the mean OXPHOS of the PBMC cells of the patients at T=0 (10,24) and T=60 days (12,40) is presented in FIG. 9, and the mean COUPLING EFFICIENCY of the PBMC cells of the patients at T=0 (3.42) and T=60 days (6.89) is presented in FIG. 10.

Example 6

Figure 11:
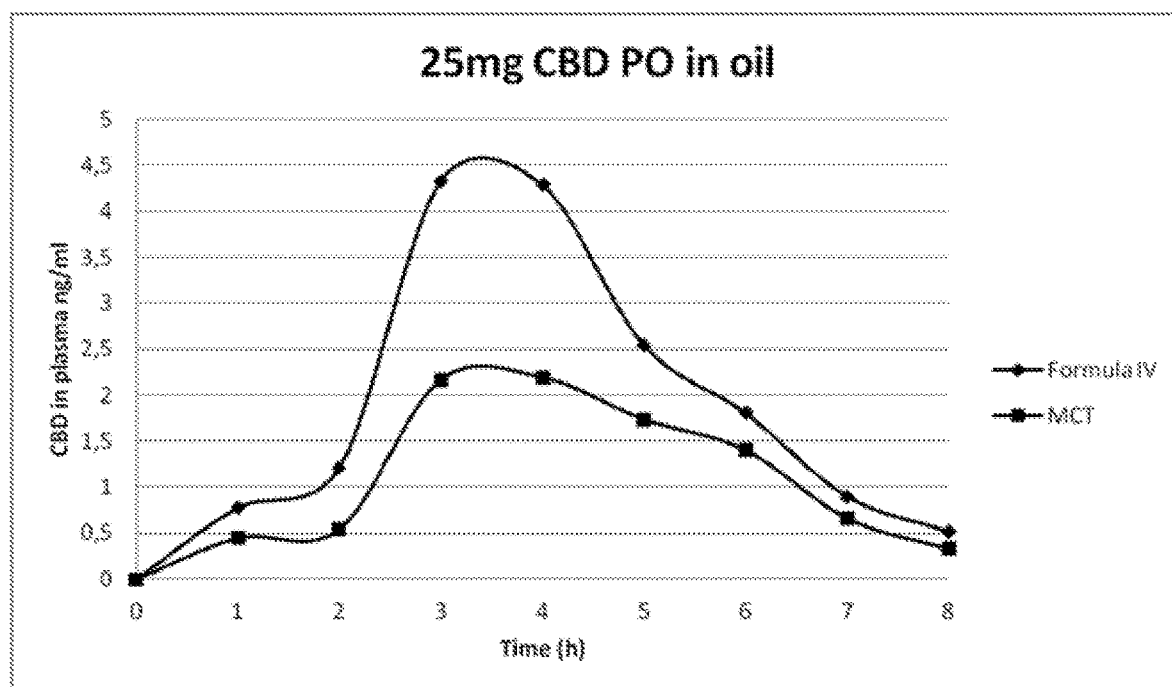
FIG. 11 shows the superiority of the compound of formula (IV) over the MCT oil on the absorption and bioavailability of CBD.

54 mg of cannabidiol (CBD) was dissolved in 2.5 g of compound of formula (IV) to give a clear solution. 1.16 g of the mixture (25 mg CBD) was encapsulated in two (2) hard gel capsules (size 00) for absorption study. A pilot absorption study was conducted in one volunteer. The two (2) hard gel capsules were swallowed with a glass of water by the volunteer fasted for 10 h. 200 ul of blood was collected by a lancet in a heparinised microtube at T=0, 1, 2, 3, 4, 5, 6, 7 and 8 h. The plasma was analyzed by HPLC/MS/MS to quantify the CBD. A comparative study was conducted with the same amount of CBD but with MCT oil (medium-chain triglycerides oil) instead of compound of formula (IV). FIG. 11 shows the superiority of the compound of formula (IV) over the MCT oil on the absorption and bioavailability of CBD.

Example 7

Figure 12:
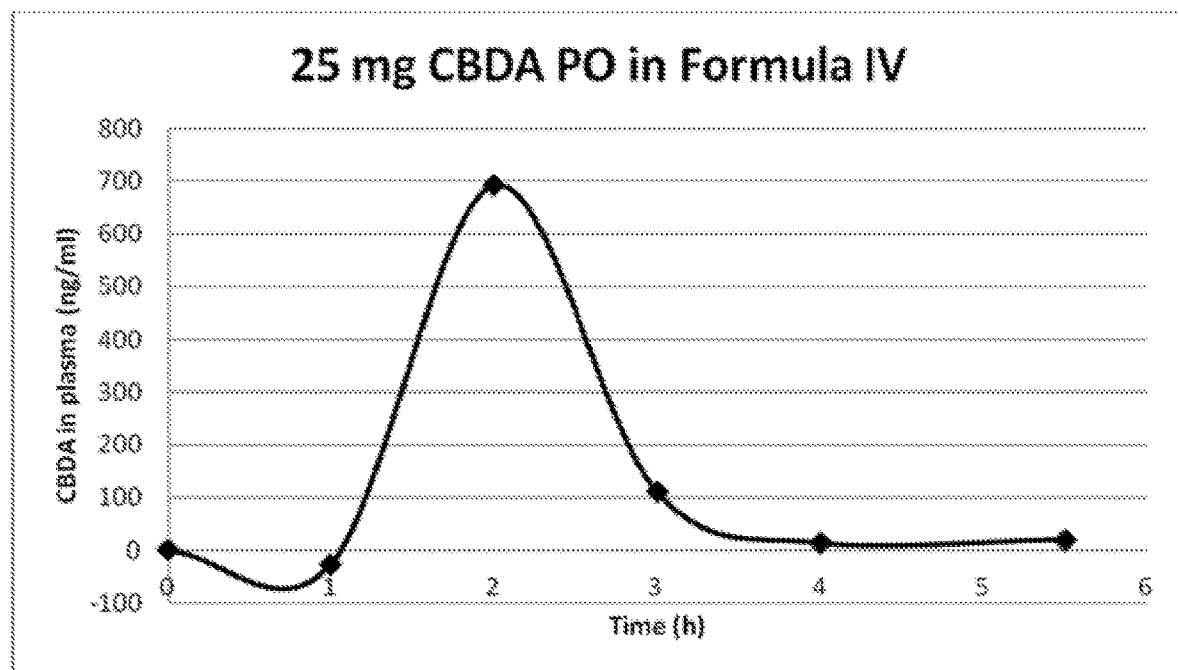
FIG. 12 shows the absorption and bioavailability profile of CBDA in plasma.

166 mg of cannabidiolic acid (CBDA) crude extract containing 20% CBDA was dissolved in 1.33 g of compound of formula (IV) to give a clear solution. 1.00 g of the mixture (25 mg CBDA) was encapsulated in two (2) hard gel capsules (size 00) for absorption study. A pilot absorption study was conducted in one volunteer. The two (2) hard gel capsules were swallowed with a glass of water by the volunteer fasted for 10 h. 200 ul of blood was collected by a lancet in a heparinised microtube at T=0, 1, 2, 3, 4, 5, 6, 7 and 8 h. The plasma was analyzed by HPLC/MS/MS to quantify the CBDA. FIG. 12 shows the absorption and bioavailability profile of CBDA in plasma.

Example 8

Figure 13:
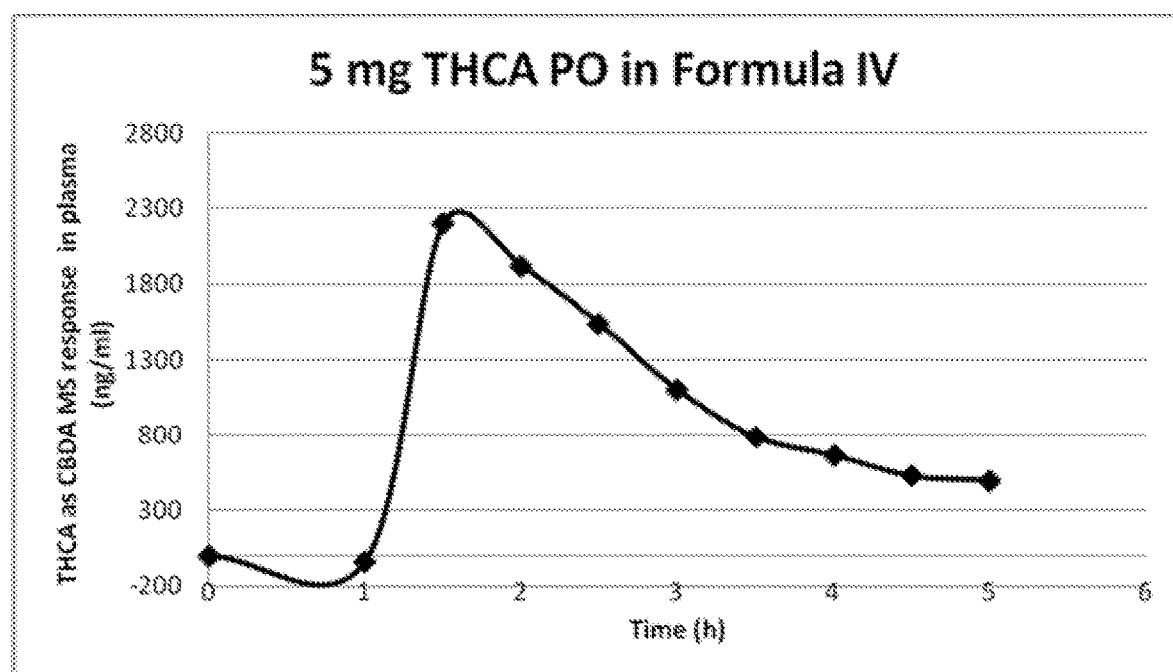
FIG. 13 shows the absorption and bioavailability profile of THCA in plasma.

106 mg of tetrahydrocannabinolic acid (THCA) crude extract containing 20% THCA was dissolved in 4.00 g of compound of formula (IV) to give a clear solution. 1.00 g of the mixture (5 mg THCA) was encapsulated in two (2) hard gel capsules (size 00) for absorption study. A pilot absorption study was conducted in one volunteer. The two (2) hard gel capsules were swallowed with a glass of water by the volunteer fasted for 10 h. 200 ul of blood was collected by a lancet in a heparinised microtube at T=0, 1, 2, 3, 4, 5, 6, 7 and 8 h. The plasma was analyzed by HPLC/MS/MS to quantify the THCA (the calibration curve was made with CBDA). FIG. 13 shows the absorption and bioavailability profile of THCA in plasma.

While the compounds, compositions, methods and uses thereof have been described in connection with specific embodiments thereof, it will be understood that they can be further modified and this application is intended to cover any variations, uses, or adaptations of the compounds, compositions, methods and uses thereof following, in general, the principles described in the present document and including such departures from the present disclosure as come within known or customary practice within the art to which the present document pertains and as may be applied to the features hereinbefore set forth, and as follows in the scope of the appended claims.

What is claimed is:

1. A composition consisting essentially of synthetic SN1 monoglyceride of fish oil, a synthetic diglyceride of fish oil selected from the group consisting of SN 1,2 synthetic diglyceride and SN 1,3 synthetic diglyceride, isolated cannabidiolic acid, synthetic ethyl ester of fish oil and glycerol.

* * * * *